US010358669B2

(12) United States Patent
Desbarats et al.

(10) Patent No.: US 10,358,669 B2
(45) Date of Patent: Jul. 23, 2019

(54) APPARATUS AND METHOD FOR REDUCTION OF PHENOL IN ENZYMATIC SOLUTIONS AND/OR FEEDSTOCK

(71) Applicants: Andrew Desbarats, Aurora (CA); Vincent Yacyshyn, Calgary (CA)

(72) Inventors: Andrew Desbarats, Aurora (CA); Vincent Yacyshyn, Calgary (CA)

(73) Assignee: IMMORTAZYME CO., Calgary, Alberta (CA)

( * ) Notice: Subject to any disclaimer, the term of this patent is extended or adjusted under 35 U.S.C. 154(b) by 220 days.

(21) Appl. No.: 15/034,893

(22) PCT Filed: Nov. 7, 2014

(86) PCT No.: PCT/CA2014/000798
§ 371 (c)(1),
(2) Date: May 6, 2016

(87) PCT Pub. No.: WO2015/066797
PCT Pub. Date: May 14, 2015

(65) Prior Publication Data
US 2016/0298155 A1    Oct. 13, 2016

Related U.S. Application Data

(60) Provisional application No. 61/901,180, filed on Nov. 7, 2013, provisional application No. 62/045,043, filed on Sep. 3, 2014, provisional application No. 62/055,063, filed on Sep. 25, 2014.

(51) Int. Cl.
| | | |
|---|---|---|
| *C12P 19/14* | (2006.01) | |
| *C12P 19/02* | (2006.01) | |
| *C12P 7/06* | (2006.01) | |
| *C12M 1/00* | (2006.01) | |
| *C12M 1/40* | (2006.01) | |
| *C12M 1/34* | (2006.01) | |
| *C12N 9/42* | (2006.01) | |
| *C12P 7/10* | (2006.01) | |

(52) U.S. Cl.
CPC ............ *C12P 19/14* (2013.01); *C12M 21/12* (2013.01); *C12M 21/18* (2013.01); *C12M 41/00* (2013.01); *C12M 41/32* (2013.01); *C12N 9/2437* (2013.01); *C12P 7/06* (2013.01); *C12P 7/10* (2013.01); *C12P 19/02* (2013.01); *Y02E 50/16* (2013.01); *Y02E 50/17* (2013.01)

(58) Field of Classification Search
CPC .. C12P 7/06; C12P 19/00; C12P 19/02; C12P 19/14; C12P 2201/00; C12P 7/10; B01D 21/26; C12N 9/2437; C12M 21/12; C12M 21/18; C12M 41/00; C12M 41/32; Y02E 50/16; Y02E 50/17

USPC .......................................... 435/68.1; 530/350
IPC ............... C12M 1/34; C12P 7/06,19/00, 19/02, 19/14, 21/00, 7/10; B01D 15/08, 21/26; C12N 9/42

See application file for complete search history.

(56) References Cited

U.S. PATENT DOCUMENTS

| 4,485,016 | A | 11/1984 | Hopkins | |
|---|---|---|---|---|
| 7,145,031 | B1 | 12/2006 | Arcangeli | |
| 7,892,805 | B2 | 2/2011 | Saville | |
| 8,349,591 | B2 * | 1/2013 | Desbarats | ............ C12N 9/2408 435/161 |
| 8,741,855 | B2 | 6/2014 | Quave | |
| 2013/0118590 | A1 | 5/2013 | Desbarats | |

FOREIGN PATENT DOCUMENTS

| WO | 2010/045168 | | 4/2010 | |
|---|---|---|---|---|
| WO | WO-2020/045168 | * | 4/2010 | |
| WO | WO 2013/000088 A1 | * | 1/2013 | ................ C02F 1/04 |
| WO | 2016/033680 | | 3/2016 | |

OTHER PUBLICATIONS

Ximenes et al. 2011. Deactivation of cellulases by phenols. Enzyme and Microbial Technology, vol. 48, pp. 54-60. (Year: 2011).*
Zawistoska et al. 1988. Immobilized Metal Affinity Chromatography of Wheat of αamylases. Cereal chemistry, vol. 65, No. 5, pp. 413-416. (Year: 1988).*
Written Opinion issued in PCT/CA2014/000798, dated Mar. 13, 2015, pp. 1-8.
International Search Report issued in PCT/CA2014/000798, dated Mar. 13, 2015, pp. 1-6.
Jonsson, et. al."Biconversion lignocellulose: inhibitors and detoxification," Biotech Biofuels, Jan. 28, 2013, vol. 6(16) pp. 1-10.
Kim, et. al., "Soluble inhibitors/deactivators of cellulose enzymes from lignocellulosic biomass," Enzyme Microb. Tech. 2011, vol. 48, pp. 408-415.
Yang, et al., "Enzymatic hydrolysis of cellulosic biomass," Biofuels, 2011, vol. 2(4), pp. 421-450.
Sutton, "A novozymes short report: fermentation inhibitors," Nvozymes, 2011, online, retrieved Mar. 2, 2015, http://bioenergy.novozymes.com/Documents/Ferm_SR_Inhibitors.pdf.
Yennamalli, et. al., "Endogluconases: insights into thermostability for biofuel applications," Biotech. Biofuels, Sep. 27, 2013, vol. 6(136), pp. 1-9.

(Continued)

*Primary Examiner* — Satyendra K Singh

(74) *Attorney, Agent, or Firm* — Jeffrey S. Melcher; Melcher Patent Law PLLC

(57) ABSTRACT

Provided are an apparatus and method for reducing the phenol concentration in a commercial enzyme solution and/or feedstock.

23 Claims, 2 Drawing Sheets

(56) References Cited

OTHER PUBLICATIONS

J Agric Food Chemistry 2013, 61, pp. 1477-1486, Barrett "Inhibition of alpha-amalyase . . . ".
J. Am Leather Chem. Assoc 2003, 98, pp. 273-278.
Kulkarni et. al., International Journal of Scientific and Research Publications, vol. 3, Issue 4, Apr. 2013.
Howell, "A-type cranberry proanthocyanidins and uropthogenic bacterial anti-adhesion activity," Phytochemistry, 66, pp. 2281-2291, (2005).
Ximenes et al.: 'Lignocellulose pretreatment: Beneficial and non-beneficial effects prior to enzyme hydrolysis' [online], American Chemical Society Meeting Paper, San Diego, Mar. 25, 2012, Retrieved from the Internet: <http://www.purdue.edu/Iorre/presentations/Eduardo%20ACS %203 .25 .12 .pdf.
International Search Report issued in PCT/CA2015/000482, dated Dec. 21, 2015, pp. 1-2. Copy is attached to WO2016/033680.
International Search Report issued in PCT/CA2015/000482, dated Dec. 21, 2015, pp. 1-3.
Written Opinion issued in PCT/CA2015/000482, dated Dec. 21, 2015, pp. 1-6.

\* cited by examiner

APPARATUS AND METHOD FOR REDUCTION OF PHENOL IN ENZYMATIC SOLUTIONS AND/OR FEEDSTOCK

FIELD OF THE INVENTION

The invention relates to an apparatus and method of reducing just-in-time the phenol levels in enzymatic solutions to enhance enzymatic activity in industrial bioprocessing. The invention further relates to a method for extracting the phenols from a biological Feedstock and recovering and purifying these extracted phenols.

BACKGROUND OF THE INVENTION

Polyphenols have shown an ability to reduce the activity of endoglucanases (amylases) in biologic solutions. J Agric Food Chemistry 2013, 61, pages 1477-1486. The mechanism of the reduction of endoglucanase activity appears to be due to the ability of polyphenols to associate with proteins through interactions with hydroxyl groups, carbonyl groups, or aromatic rings. J. Am Leather Chem. Assoc 2003, 98, pages 273-278. It has also been hypothesized that polyphenols inhibit the Maillard reaction by tying up or quenching some feed stock sugars and other transient reaction products that the reaction needs to proceed. Dr. Devin Peterson, National Meeting of the American Chemical Society, Washington, D.C., Sep. 1, 2005. These findings may have implications regarding the efficacy of sugar conversion in commercial bioreactors.

However, the reduction of phenol levels decreases stability of enzymatic formulations and biogel formation becomes a significant problem. U.S. Pat. No. 8,741,855 discloses that polyphenol compositions allow for stabilization of solutions and the inhibition of the formation and growth of biofilms and consequent bacterial infection.

U.S. Pat. No. 8,349,591, the complete disclosure of which is incorporated herein by reference, discloses a method of enhancing enzyme activity. However, this patent does not disclose reducing phenol concentration.

Phenol concentrations have been reduced in waste water. Although the use of various agents such as peroxidase is well known for the treatment of wastewater, for example U.S. Pat. No. 4,485,016 and article by Kulkarni et. al., International Journal of Scientific and Research Publications, Vol. 3, Issue 4, April 2013, no data or experimentation is available as to whether these methods are suitable for the use to remove phenols from organic solutions in order to alter/enhance the activities of enzymes contained in these solutions.

Bioreactors are now well known. In general, a bioreactor is a vessel in which a biochemical reaction takes place. Commercial-scale bioreactors typically have a capacity of over 1000 gallons. In commercial scale ethanol plants, bioreactors in which starch and cellulose are hydrolysed with enzymes typically have a capacity of 20,000 to 100,000 gallons. Fermentation vessels, within which enzymes catalyze biochemical reactions and microorganisms use reaction intermediates to produce metabolites, typically have a capacity of 100,000 to 1,000,000 gallons. Conditions such as temperature, pressure, pH and solution viscosity are tightly controlled within bioreactors due to the sensitivity of biochemicals and microorganisms. For example bioreactors within which starch and cellulose are hydrolysed typically have temperatures in the range of 75 to 100 degrees Celsius for starch and 45 to 75 degrees Celsius for cellulose.

Commercial enzyme preparations typically contain a high concentration of enzymes, between 5 mg/mL and 25 mg/mL. These commercial enzyme preparations, have the benefit of reducing the number of shipments and the required storage capacity in facilities that use industrial enzymes.

Liquid enzyme formulations are often dosed at 3 places in an ethanol plant;
1) The slurry system, where initial hydrolysis takes place. In a typical 40 million gallon per year dry-mill ethanol plant, alpha-amylase is often added at between 500 mg/min and 1200 mg/min.
2) The liquefaction system, where secondary hydrolysis takes place. In a typical 40 million gallon per year dry-mill ethanol plant, alpha-amylase is often added at between 1000 mg/min and 2000 mg/min.
3) The fermentation system, where final hydrolysis and fermentation of the product takes place. In a typical 40 million gallon/year dry-mill ethanol plant, the enzyme dose is in the range of between 60 and 120 Gallons in a 500,000 Gallon fermenter.

These dose ranges are adjusted accordingly for different plant capacities. For instance, 100 million gallon per year dry-mill ethanol plants require an alpha amylase dose in the range of 1250 mg/min and 3000 mg/min in the slurry system and between 2500 mg/min and 5000 mg/min in slurry and liquefaction respectively.

In addition, ethanol plants may produce ethanol from different types of feedstock. These feedstocks will vary in terms of the amount of ethanol produced per ton of feedstock. For example, dry mill ethanol plants typically produce between 2.5 and 2.9 Gallons per bushel of corn. The corn is milled and mixed with water in a ratio of between 28% and 38% solids. The theoretical ethanol yield for a ton of corn stover is 113 Gallons per dry ton. Currently, solids ratios for ethanol production from biomass sources such as corn stover are lower than solids ratios for ethanol production from corn and other grains and is typically between 8 and 20% solids.

However, at high enzyme concentrations it is difficult to accurately dose low volumes of enzyme since, in the case of a 25 mg/mL protein, each milliliter contains 25 mg of protein, which may be more than one wants to dose over a particular time frame.

Phenols, such as hydroxycinnamic acid, hydroxybenzoic acid and other hydrolysable and condensed tannins are commercially valuable. The health benefits of these compounds are well documented. There is therefore value in isolating these phenols after removing them from a feedstock. A stream of purified phenols could provide an additional revenue stream for feedstock processors such as alcohol producers, sugar producers and oil seed processors.

Howell et al. have described a method by which proanthocyanidin, a hydrolysable tannin from cranberry, can be extracted with acetone and purified using a C-18 solid phase chromatography column. This method has been used by Kim et al. to isolate tannins that have been extracted from lignocellulosic biomass.[i]

SUMMARY OF THE INVENTION

A primary object of the present invention is to provide an apparatus and method for removing or reducing the concentration of phenols in biological solutions containing enzymes. Some examples of such operations are the use of enzymes in the processing of High Fructose Corn Syrup, ethanol, butanol, and other grain based processes or cellulose.

It is a further object of the process to reduce phenol levels in biologic solutions which will lead to enhanced enzyme activity. Phenol concentrations in commercial enzyme solutions are at least 20 mg/L.

It is a further object of the present invention that "just-in-time" reduction of phenol levels will allow for optimization of enzyme activity on a commercial basis.

These objectives and other objectives can be obtained by a method of producing alcohol or sugar in a commercial-scale bioreactor comprising:

reducing the phenol concentration of commercial enzyme preparation comprising at least one endoglucanases or cellulase to form a phenol-reduced enzyme preparation having a desired phenol concentration level; and within 100 hours of production of the phenol-reduced enzyme solution, transferring at least a portion of the phenol-reduced enzyme solution to a commercial-scale bioreactor containing at least 20,000 gallons of at least one of starch or cellulose to produce an alcohol or sugar, wherein a total amount of enzyme in the form of the phenol-reduced enzyme solution added to the bioreactor is at least 20% less than the amount of enzyme in the form of the commercial enzyme preparation that would have been required to produce an equivalent amount of alcohol or sugar.

These objectives can also be obtained by an apparatus for producing alcohol or sugar in a commercial-scale bioreactor, the apparatus comprising:

a mixing vessel;

a mixing device for mixing a solution in the mixing vessel;

a source of stabilized commercial enzyme solution in communication with the mixing vessel;

a phenol reducing material in communication with the mixing vessel;

a storage vessel in communication with the mixing vessel; and at least one commercial-scale bioreactor having a capacity of at least 20,000 gallons in communication with the storage vessel.

The objectives can further be obtained by a method of producing alcohol or sugar in a commercial-scale bioreactor comprising:

reducing the phenol concentration of a feedstock prior to or during application of an enzyme to the feedstock for converting the feedstock to an alcohol or sugar.

The phenolic compounds adsorbed to adsorbent or solubilised by solvent can be separated from the biological feedstock downstream from the bioreactor by screening appropriate for the particle sizes of the biological feedstock and the particle size of the adsorbent media, centrifugation, decanting and/or hydrocycloning.

Phenolic compounds can be desorbed from the adsorbent media using various methods. The preferred method is acetone extraction where 70% aqueous acetone is added to the adsorbent material containing bound phenolic and enzyme inhibitor compounds. After ultrasonication and centrifugation, the liquid phase is removed as per the method of Makkar. The solid residual from the centrifugation step can be reused to adsorb additional phenolic and enzyme inhibitor components.

After removal of acetone, the fraction rich in tannins can be subjected to column chromatography to separate the various phenol components. Chromatography can be selected from ion-exchange, size exclusion, reverse phase, affinity or a combination of these. The preferred separation method uses a C-18 reverse phase column following the methods of Howell (A-type cranberry proanthocyanidins and uropathogenic bacterial anti-adhesion activity. Phytochemistry, 66, 2281-2291).

DETAILED DESCRIPTION OF THE INVENTION

Figure 1:
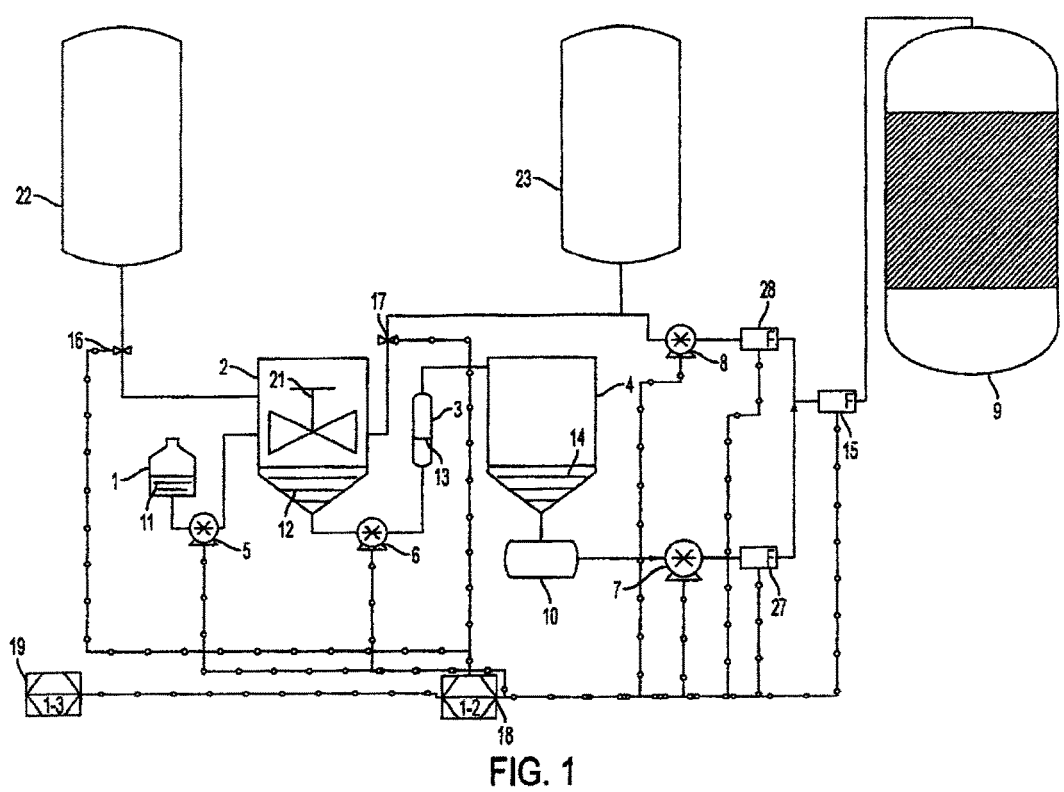
FIG. 1 shows a side view of an apparatus for reducing just-in-time the phenol concentration in an enzyme solution.

When used on a full scale production run, phenol-reduced enzyme solutions result in significant unexpected increases in enzyme activity. In the production environment equivalent sugar production, as measured by fermentation profiles, indicate that the claimed process improves the rate at which substrate is converted to product per unit mass of enzyme used. Use of the word phenol refers to both a single type of phenol or polyphenol, mixtures of phenols, and/or mixtures of polyphenols. The term phenol also includes any feedstock compound containing a phenol or polyphenol moiety.

On a commercial scale, the present invention provides a reduction of at least 20%, preferably at least 40%, and more preferably at least 60%, of the total amount of enzyme in the form of the phenol-reduced enzyme solution added to the bioreactor compared to the amount of enzyme in the form of the commercial enzyme preparation that would have been required to produce an equivalent amount of alcohol or sugar.

Commercial stabilized enzyme preparations are now well known, such as those provided by Novozymes, Dupont, and BASF. Improving enzyme function in the bioreactor by reducing the phenol concentration prior to addition to the bioreactor can be effected according to the present invention using any desired commercial enzyme solution. Preferably, the enzyme comprises at least one group 3 hydrolase. A most preferred enzyme is amylase.

Typical commercial enzyme preparations contain a high concentration of polymeric compounds, dissolved salts, antioxidants, substrates and/or substrate analogs. These compounds stabilize commercial enzyme preparations in order for enzyme users to store large quantities on site, reduce transportation costs involved in shipping small quantities and ensure minimal bacterial growth over long periods of time. However, commercial stabilized enzyme preparations must often be delivered accurately to bioreactors containing aqueous mixtures. It has been found that hydration of these commercial stabilized enzyme solutions according to the present invention can improve dosing accuracy and reduce the mass of enzyme required in the bioreactor.

Alpha-amylase enzymes are used at temperatures ranging from 75 to 95 degrees C. for the hydrolysis of starch and long-chain maltodextrins. As a result of the process described in the present invention, the phenol-reduced alpha-amylase enzyme is more resistant to thermal and chemical denaturation than the commercial stabilized enzyme from which it is derived. As a result, the phenol reduced alpha-amylase with lower activity relative to the commercial stabilized enzyme solution from which it was derived, resists denaturation and is active for longer at high temperatures. Enzyme users therefore can reduce the amount of alpha-amylase used in high-temperature bioreactors. This is especially relevant for liquefaction bioreactors in dry-mill fuel ethanol plants were the residence time of the substrate is often more than one hour. By using the present invention, users of these commercial enzyme formulations can substantially reduce the cost of operating these bioreactors.

The invention will now be explained with reference to the attached figure without being limited thereto.

As shown in FIG. 1, the phenol reducing apparatus comprises an optional buffer vessel 1, a mixing vessel 2, optional column(s) 3 containing a phenol reducing material 13, a storage vessel 4, an optional surge tank 10. The mixing vessel 2, the storage vessel 4, and surge 10 can be constructed of 304 or 316 stainless steel but can be constructed of any desired material suitable to hold the solutions.

The buffer vessel 1 contains a polymeric compound or a mixture of water and polymeric compound. The desired final concentration of polymeric compound in mixing vessel 2 can be, for example between 2% by volume and 15% by volume, preferably between 5% and 10% by volume. The polymeric compound 11 can be pumped using a variable speed pump 5 to the mixing vessel 2 containing the necessary quantity of water 22 to obtain the desired final concentration of polymeric compound. Once the final concentration of buffer is reached in mixing vessel 2, commercial enzyme preparation 23 is added to mixing vessel 2. Optionally the mixture of polymeric compound 11, water 22 and commercial stabilized enzyme preparation 23 can be mixed for between 0.5 minutes and 10 minutes, preferably between 2 minutes and 5 minutes with a stainless steel impeller 21. Any desired mixing device may be used in place of the impeller 21 as desired.

Commercial enzyme preparation 23 is preferably diluted in the mixing vessel with, for example, between 4 parts polymeric compound and water to 1 part commercial enzyme preparation and 100 parts polymeric compound and water to 1 part commercial enzyme preparation, preferably between 4 parts polymeric compound and water to 1 part commercial enzyme preparation and 15 parts polymeric compound and water to 1 part commercial enzyme preparation.

The dilution ratio depends on the concentration of enzyme in the commercial enzyme preparation. Currently, concentrations of enzyme used in commercial enzyme preparations for the fuel ethanol, high fructose corn syrup and other industrial applications range from approximately 1% to 20% enzyme. In the future, higher concentrations of enzymes in commercial enzyme preparations may be used. As these concentrations increase, so too will the dilution ratio. For example, a commercial enzyme preparation with a 75% enzyme concentration may enable a dilution ration where 250 parts polymeric compound and water are mixed with 1 part commercial enzyme preparation.

The concentration of the phenol can be reduced in the mixing vessel 2 or by passing the commercial enzyme solution or diluted enzyme solution through a separate device(s), such as one or more column(s) 3, which can be in any combination of series or parallel configurations, containing one or more phenol reducing material(s) 13.

In a preferred embodiment, the mixture of polymeric compound 11 and commercial enzyme preparation 23 can be metered, using variable speed pump 6 through a column(s) 3 containing a phenol reducing material 13 such that the residence time of the dilute polymeric compound-enzyme mixture in the column is, for example, between 1 and 15 minutes, preferably between 5 and 10 minutes. Examples of the phenol reducing material include, activated carbon, metal-impregnated particulate matter can be zeolite, amberlite, plastic pellets, ceramic beads, glass beads or any other material upon which metal particulate matter can be impregnated. Preferred metals include zinc, silver, copper, nickel, KDF55 and KDF85. The most preferred is KDF55. In a preferred embodiment, spent KDF55 is replaced with fresh KDF55 after between 250 gallons and 750 gallons of phenol-reduced enzyme solution. Passing through the column(s) 3 reduces the phenol concentration of the enzyme solution and the phenol-reduced enzyme solution 14 is collected in storage vessel 4. An optional surge tank 10 can be connected to the storage vessel 4 so that the storage vessel 4 can be emptied as desired. Depending on the rate at which the enzyme is phenol-reduced and the rate at which the phenol-reduced enzyme solution is added to the bioreactor 9, the phenol-reduced enzyme solution may sit in the storage vessel 4 for up to 100 hours.

Phenol-reduced enzyme solution can be pumped to the bioreactor with a variable speed pump 7. The phenol-reduced enzyme solution 14 can be sent to the bioreactor 9 alone or in combination with the commercial stabilized enzyme preparation 23. The ratio of phenol-reduced enzyme solution and commercial stabilized enzyme preparation can be between 100% phenol-reduced enzyme solution to 0% stabilized enzyme preparation and 10% phenol-reduced enzyme solution to 90% stabilized enzyme preparation, preferably 80% phenol-reduced enzyme solution to 20% stabilized enzyme preparation. The percentages used herein refer to the percent of non-phenol-reduced enzyme used in a particular bioreactor prior to introduction of the present invention.

Two variable drive pumps 7 and 8 can be in communication with each other and with flowmeters 27 and 28 to ensure delivery of adequate amount of phenol-reduced enzyme to the bioreactor 9. For example, if there is a problem with variable drive pump 7, then the flowmeter 27 would communicate to the control system 18 the extent to which flow from pump 7 had slowed. Control system 18 then instructs variable drive pump 8 to take over to an extent that compensates for the decrease in flow from pump 7. This ensures that an adequate quantity of enzyme, either phenol-reduced or non-phenol-reduced, is continuously delivered to bioreactor 9. The apparatus can be designed such that a stabilized commercial enzyme preparation can be supplied to the apparatus by a valve 17 and supply is independent of the variable drive pump 8. If there is a problem with variable drive 8, commercial stabilized enzyme can be delivered to the apparatus to continue reducing the phenol concentration of the enzyme and delivering it to bioreactor 9.

The control system 18 for the apparatus contains programmed settings for automated control of all valves and pumps associated with the apparatus and process. A computer screen provides visual cues to operators for tasks to complete such as changing the phenol-reducing material 13 in the column(s) 3 and cleaning the storage tank 4.

In another embodiment of the present invention, the phenol-reduced enzyme solution 14 is pumped through one or more column(s) 3, which can be in any combination of series or parallel configurations, containing a phenol reducing material(s) 13 and directly fed into a bioreactor, without being stored in a storage vessel 4, as in a continuous process.

In another embodiment of the present invention, the polymeric compound and water mixture are mixed with stabilized enzyme preparation 23 in-line, using an in-line mixer and pumped directly through the column(s) 3 containing phenol-reducing material 13 to the bioreactor, without being mixed in a mixing vessel 2 and without being stored in a storage vessel 4.

In another embodiment of the present invention, control system 18 is in communication with a central control system 19 that monitors the entire production facility. Changes in conditions within the production facility can trigger changes in the control system for the apparatus of the current invention. For example, in a fuel ethanol plant, a feedstock change from corn to milo, or from switchgrass to municipal solid waste, or corn stover, could result in changed requirements for enzyme to feedstock ratios. These ratio changes may be preset in the control system for the present apparatus. As these changes are captured in the facility data control system, automatic adjustments to the dosing regime, component inputs and ratios of phenol-reduced enzyme to commercial stabilized enzyme can be made.

Extraction and purification of the phenolic compounds are described with reference to FIG. 2, without being limited thereto. The process steps in FIG. 2 are listed below:

A=Process Stream containing milled grain and/or milled and/or pre-processed fiber and other process solids B=Adsorbent with binding affinity for phenols, tannins and other enzyme inhibitors C=Process Stream with adsorbent resulting from the addition of B to A D=Outflow from a bioreactor comprising the adsorbent and the components from the reactions in the bioreactor (phenol-reduced feedstock)

E=Overflow comprising adsorbent bound to phenols, tannins and other enzyme inhibitors F=Underflow comprising slurry containing biomolecules for use in downstream processing G=Desorbed phenols, tannins and other enzyme inhibitors resulting from washing the adsorbent H, I, J=Purified phenols, tannins and enzyme inhibitors for use in downstream applications The adsorbent B in FIG. 1 is a particle larger than the other process solids contained in A. After adsorbing the tannins, phenols and other enzyme inhibitors in the Bioreactor, the overflow from the screen E contains the large adsorbent particles with tannins, phenols and other enzyme inhibitors bound. The smaller particles containing process solids and other dissolved components F are used in downstream processing. After washing the adsorbed chemicals comprising tannins, phenols and other enzyme inhibitors G from the adsorbent B, column chromatography is used to separate the tannins, phenols and other enzyme inhibitors to purify them for downstream applications.

Figure 2:
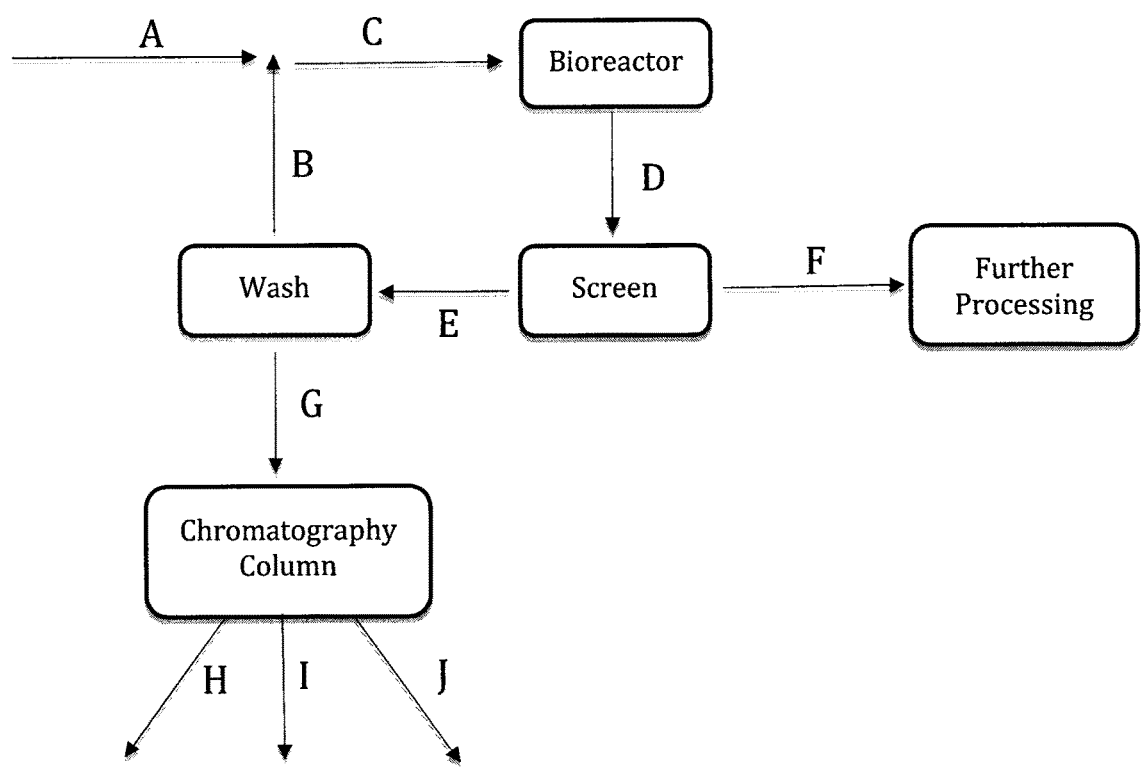
FIG. 2 shows a schematic for the extraction and recovery of phenolic compounds from a feedstock

Granular activated carbon B with a mesh size of 4×8 is added to a mixture of water, 15% (w/v) corn mash and 15% sorghum mash (w/v) A with a mean particle size of 700 μm and forming a mixture of water, corn and sorghum mash and granular activated carbon C and processed according to FIG. 2. The granular activated carbon and corn/sorghum mash mixture C remain in the bioreactor for approximately 150 minutes. The resulting effluent D from the bioreactor is subjected to screening on an 850 μm screen to separate the solids. The underflow, stream F, comprises smaller solids consisting of corn and sorghum mash and associated biochemicals. The larger solids, E, comprising granular activated charcoal and adsorbed phenols and enzyme inhibitors are retained on the screen as overflow. The phenolic compounds are desorbed from the granular activated carbon in stream E by acetone extraction. The regenerated granular activated carbon B is returned to the bioreactor. The acetone-extracted phenolic compounds G are separated on a chromatography column to produce various purified fractions H, I, J.

The pH should be maintained at or around the optimum pH of the enzyme. For alpha-amylase we have found that a pH between 5.5 and 6.5 is suitable, most preferably a pH of between 5.75 and 6.0. When using the present invention with alpha-amylases that have a lower pH range, the pH will be maintained in this lower range, for example 4.5 to 5.5. For glucoamylase, we have found that a pH between 4.2 and 5.0 is suitable, most preferably a pH of between 4.5 and 4.9. For cellulase, we have found that a pH between 5.5 and 6.5 is suitable, most preferably a pH of between 5.8 and 6.3.

The temperature for the process can be any temperature at which the enzyme in question is active. The method is carried out most preferably at ambient temperature. To extend the life of the phenol-reduced enzymes, the method can be carried out at temperature lower than ambient temperatures, most preferably at 4 degrees Celsius.

The bioreactor conditions may play an important role in the effectiveness of the present invention. Use of the present invention is more effective in bioreactors where the substrate is soluble in aqueous solution. For example, in the production of fuel ethanol, reducing the phenol concentration of alpha-amylase according to the present invention is more effective in the liquefaction system where substrate is predominantly soluble, long-chain maltodextrins as compared to the slurry system where the substrate is predominantly insoluble starch granules. While effectiveness is relatively lower in the slurry, there is still an advantage to adding some phenol-reduced alpha-amylase to the slurry system in combination with non-phenol-reduced commercial enzyme preparation.

The present invention, as described above provides a process and an apparatus to overcome difficulties faced by users of commercial enzyme preparations relating to high concentrations of polymeric stabilizers, salts and antioxidants and the related mechanical difficulties of accurately pumping high specific gravity solutions to bioreactors. Overcoming these difficulties must be done in a just-in-time fashion to eliminate negative effects, such as bacterial growth and enzyme agglomeration, related to reformulating these commercial enzyme preparations.

Lab scale analysis demonstrates a significant reduction in phenol levels in commercial enzyme solutions. These phenols may be present due to residual feedstock, metabolism of fermenting micro-organisms producing enzymes, or additives to stabilize the commercial enzyme solutions. Those skilled in the art, would not remove such phenols prior to use of these enzymes in a commercial bioreactor. The present invention identifies phenols in lab assays, and correlated their reduction with commercially enhanced activity of enzyme solutions.

The phenol concentration the commercial enzyme solution is preferably reduced by at least 30%, more preferably by at least 50%, and most preferably by at least 95%. Preferably, the phenol concentration is reduced to less than 50 ppm, more preferably less than 20 ppm, more preferably less than 10 ppm, and most preferably less than 5 ppm. The phenol concentration is preferably reduced to level that provides an enzyme activity such that at least 20%, preferably at least 40%, and more preferably at least 60%, of the total amount of enzyme in the form of the phenol-reduced enzyme solution added to the bioreactor compared to the amount of enzyme in the form of the commercial enzyme preparation that would have been required to produce an equivalent amount of alcohol or sugar.

Although metal or metal impregnated materials have been used previously as in U.S. Pat. No. 8,349,591, this patent does not disclose reducing the phenol concentration in a commercial enzyme solution, nor by how much the phenol concentration should be reduced. Similarly, while carbon black has been used to increase enzyme activity in the past, there has been no teaching of using carbon black to reduce phenol concentration in a commercial enzyme solution, nor by how much the phenol concentration should be reduced. The metal or metal impregnated materials disclosed in the '591 patent and/or carbon black can now be used to reduce the phenol concentration to a desired level.

Examples of methods of reducing the phenol concentration include, but are not limited to, the following:

1. Polymerization—Phenol may be polymerized in the presence of peroxidase (47 to 1500 mg/L reduced by 60 to 90%). The peroxidase may be used in solution or immobilized to carbon black, silica, chitin, calcium alginate, nobel metals to reduce the phenol level.
2. Electro-coagulation—An aluminum anode and cathode can be used to adsorb phenol, such as for example by 30 mg/L by 97% in 2 hours.
3. Extraction—1-hexanol, 1-heptanol, or 1-octanol may be used in combination with an amine mixture and centrifugation to reduce phenol levels, for example by 99%.
4. Photodecomposition—Near UV irradiated aqueous $TiO_2$ solutions may be used to reduce phenol levels, for example to an order of magnitude of 70%.
5. Biological Methods—Laccases, specifically tyrosinases, or polyphenol oxidase, may be used to reduce phenol concentrations, for example 420 mg/L of phenol by 75% in a 4 hour period. The laccases may be used in solution or immobilized to carbon black, silica, chitin, calcium alginate, nobel metals.
6. Biological Methods—Phenol degrading bacteria such as *Pseudomonas Putida* can be used to reduce the phenol concentration, for example by degrading 500 to 600 mg/L of phenol after 48 hours to 0 or any other type of aerobic bacteria.
7. Electro-Fenton (EF Fere) Method—Hydrogen peroxide and electrogenerated ferrous ions may be used to reduce phenol levels.
8. Oxidation processes—Single ozonation may be used to reduce phenol levels.
9. Ion Exchange and Adsorption—Liquid-phase adsorption of phenols with silica gel, activated alumina, or activated carbon may be used to reduce phenol levels.
10. Ion Exchange and Adsorption—Aqueous solution can be used to reduce phenol concentrations by adsorption and ion exchange mechanisms onto polymeric resins
11. Membrane based separation—Ionically and covalently cross-linked ethylene-methacrylic acid copolymers may be used to reduce phenol levels.
12. "Bubble extractors" can be used to reduce phenol levels.
13. Chlorine Dioxide can be used to reduce phenol levels.
14. Supercritical CO can be used to reduce phenol levels.
15. Wet air oxidation can be used to reduce phenol levels.
16. Foam fractionation can be used to reduce phenol levels.

Phenols are considered a necessary part of commercial enzyme formulations for stability and preservation in spite of phenols now being found to have inhibitory properties. While removal of phenols is well known in water treatment processing, the phenol removal in commercial enzyme formulations was not known prior to the present invention. Thus, the use of processes for removing phenols in waste water, or other solutions, is not known for use in removing phenols in commercial enzyme formulations. Experimental data demonstrates that just-in-time removal of phenols unexpectedly increases the enzyme activity while minimizing the resultant enzyme formulation instability.

The methods of removing phenols from the enzyme formulation described herein can be used to remove or reduce the phenol concentration in a feedstock. Baseline phenolic acid concentrations are well known (phenol explorer). The phenol content in whole grain maize (hydroxycinnamic acid) is typically 0.53 mg phenol/100 g of feedstock. The phenol content in whole sorghum (hydroxybenzoic acid) is typically 2.55 mg phenol/100 g of feedstock. The phenol content in cellulose (wood products) is typically from 7 to 13% (Cellulose Chem. Technol., (9-10), pages 541-550 (2012). The methods described herein can reduce the phenol content by at least 1%, preferably at least 5%, and most preferably greater than 10%. All percentages are based on weight unless otherwise stated.

EXAMPLE 1

A phenol-reduced enzyme solution is obtained by mixing 1 part of Dupont stabilized alpha-amylase preparation with 9 parts water and 1 part propylene glycol at room temperature. This serves to reduce the concentration of polymeric stabilizers. The inclusion of propylene glycol provides enough stability so that the enzyme solution may remain in the vessel so that it may be used for up to 100 hours. Said phenol-reduced enzyme solution is then passed through a column containing KDF-55, a copper-zinc alloy, and pumped into a vessel. This solution is then pumped through a second chamber containing but not limited to one of the 16 methods above to further reduce the level of phenol present in the enzymatic solution. MS/GC samples may be used to determine the optimal reduction of phenol levels. The alpha-amylase may then be added to the slurry tank or liquefaction tank or subsequent tank for down stream processing.

Gas chromatography/mass spectroscopy data shows the concentration of phenols in a commercial enzymatic solution is typically about 50 microgram/gram. With the use of activated carbon concentration of can be reduced to 25 microgram/gram, with the residual phenol being adsorbed on the activated carbon.

EXAMPLE 2

10 ml of Dupont alpha-amylase was mixed with 1 ml of 30% hydrogen peroxide and 1.277 grams peroxidase. The phenol concentration of the resultant mixture decreased from an initial 54 ppm to less than 5 ppm.

Passing the Dupont enzyme solution through activated carbon only resulted in a 30-50% reduction in phenol levels (approximately 50 ppm to approximately 35-25 ppm).

While the claimed invention has been described in detail and with reference to specific embodiments thereof, it will be apparent to one of ordinary skill in the art that various changes and modifications can be made to the claimed invention without departing from the spirit and scope thereof.

The invention claimed is:

1. A method of producing alcohol or sugar in a commercial-scale bioreactor comprising:
   reducing phenol concentration of a commercial enzyme preparation comprising at least one group 3 hydrolase that contains phenol, to form a phenol-reduced enzyme preparation having a desired phenol concentration level, wherein the phenol concentration has been reduced to less than 50 ppm; and within 100 hours of production of the phenol-reduced enzyme preparation, transferring at least a portion of the phenol-reduced enzyme preparation to a commercial-scale bioreactor containing at least 20,000 gallons of at least one of starch or cellulose to produce an alcohol or sugar, wherein a total amount of enzyme in the form of the phenol-reduced enzyme preparation added to the bioreactor is at least 20% less than the amount of enzyme in the form of the commercial enzyme preparation that would have been required to produce an equivalent amount of the alcohol or sugar.

2. The method according to claim 1, wherein a total amount of enzyme in the form of the phenol-reduced enzyme preparation added to the bioreactor is at least 40% less than the amount of enzyme in the form of the commercial enzyme preparation that would have been required to produce an equivalent amount of the alcohol or sugar.

3. The method according to claim 1, the step of reducing the phenol concentration comprises passing the commercial enzyme preparation through a chamber containing at least one metal particulate matter or metal-impregnated particulate matter, wherein the metal impregnated on the metal-impregnated particulate matter comprises at least one of silver, zinc, nickel and copper, or wherein the metal impregnated particulate matter comprises at least one of zeolite, amberlite, plastic pellets, ceramic and glass beads.

4. The method according to claim 1, wherein reducing the phenol concentration comprises at least one of the following steps of:
   passing the commercial enzyme solution through a chamber containing activated carbon black;
   polymerizing the phenol in the presence of peroxidase;
   using an aluminum anode and cathode to adsorb phenol;
   extracting the phenol with 1-hexanol, 1-heptanol, or 1-octanol in combination with an amine mixture and centrifugation;
   photodecomposing the phenol using UV irradiated aqueous TiO2 solutions
   using a soluble or immobilized laccase, a soluble or immobilized tyrosinase, or a soluble or immobilized polyphenol oxidase;
   using a phenol degrading bacteria;
   using hydrogen peroxide and electrogenerated ferrous ions;
   using ozonation;
   using ion exchange and adsorption with silica gel, activated alumina, or activated carbon;
   using ion exchange and adsorption onto a polymeric resin;
   using a membrane based separation, wherein ionically and covalently cross-linked ethylene-methacrylic acid copolymers are used;
   using a bubble extractor;
   utilizing chlorine dioxide;
   utilizing supercritical CO;
   using wet air oxidation; or
   using foam fractionation.

5. The method according to claim 1, wherein said commercial-scale bioreactor comprises at least one of a slurry system, a pre-treatment system, a liquefaction system, a saccharification system, or a fermentation system.

6. The method according to claim 1, wherein said commercial-scale bioreactor comprises a starch or cellulose processing plant wherein the bioreactor contains at least one of starch, maltodextrin, cellulose or xylose.

7. The method according to claim 1, wherein alcohol is produced, or wherein grain syrup comprising at least one sugar is produced.

8. The method according to claim 1, wherein the phenol-reduced enzyme preparation is pumped continuously to the bioreactor from a mixing vessel and is not stored in a storage vessel.

9. The process according to claim 1, further reducing the phenol concentration of the commercial enzyme preparation comprising the at least one group 3 hydrolase and an endoglucanase or cellulase to form the phenol-reduced enzyme preparation having the desired phenol concentration level.

10. The method according to claim 1, wherein a total amount of enzyme in the form of the phenol-reduced enzyme preparation added to the bioreactor is at least 60% less than the amount of enzyme in the form of the commercial enzyme preparation that would have been required to produce an equivalent amount of the alcohol or sugar.

11. The method according to claim 1, wherein the at least one of starch or cellulose is from a feedstock and the method further comprises reducing by at least 1% a phenol concentration of the feedstock.

12. The method according to claim 11, wherein the step of reducing the phenol concentration in the feedstock comprises passing the feedstock through a chamber containing at least one metal particulate matter or metal-impregnated particulate matter resulting in a phenol-reduced feedstock and a phenol-rich particulate matter, wherein the metal impregnated on the metal-impregnated particulate matter comprises at least one of silver, zinc, nickel and copper, or wherein the metal impregnated particulate matter comprises at least one of zeolite, plastic pellets, ceramic and glass beads.

13. The method according to claim 11, wherein the step of reducing the phenol concentration of the feedstock comprises at least one of the following steps of:
   passing the feedstock through a chamber containing activated carbon black resulting in a phenol-reduced feedstock and a phenol-rich carbon black;
   polymerizing the phenol in the presence of peroxidase;
   using an aluminum anode and cathode to adsorb phenol;
   reducing the phenol concentration comprises extracting the phenol with 1-hexanol, 1-heptanol, or 1-octanol in combination with an amine mixture and centrifugation resulting in a phenol-reduced feedstock and a phenol-rich extract;
   photodecomposing the phenol using UV irradiated aqueous TiO2 solutions;
   using a soluble or immobilized laccase, a soluble or immobilized tyrosinase, or a soluble or immobilized polyphenol oxidase;
   using a phenol degrading bacteria;
   using hydrogen peroxide and electrogenerated ferrous ions;
   using ozonation;
   using ion exchange and adsorption with silica gel, activated alumina, or activated carbon;
   using ion exchange and adsorption onto a polymeric resin;
   using a membrane based separation, wherein ionically and covalently cross-linked ethylene-methacrylic acid copolymers are used;
   using a bubble extractor;
   utilizing chlorine dioxide;
   utilizing supercritical CO;
   using wet air oxidation; or
   using foam fractionation.

14. The method according to claim 11, wherein an alcohol or wherein a grain syrup comprising at least one sugar is produced.

15. The method according to claim 11 comprising:
reducing the phenol concentration of the feedstock by exposing said feedstock to media that adsorbs or preferentially solubilizes phenolic compounds to create a phenol-reduced feedstock and a phenol-rich fraction;
subjecting said phenolic-rich fraction and phenol-reduced feedstock to at least one of hydrocycloning, screening, decanting or centrifugation to separate the phenol-reduced feedstock from the phenol-rich fraction; and
washing said phenol-rich fraction to extract the phenolic compounds from the adsorbate or solvent and forming a fraction rich in phenolic compounds and a fraction of phenol-reduced adsorbate or phenol-reduced solvent.

16. The method according to claim 15, the step of reducing the phenol concentration in the feedstock comprises passing the feedstock through a chamber containing at least one metal particulate matter or metal-impregnated particulate matter, wherein the metal impregnated on the metal-impregnated particulate matter comprises at least one of silver, zinc, nickel and copper, or wherein the metal impregnated particulate matter comprises at least one of zeolite, plastic pellets, ceramic and glass beads.

17. The method according to claim 16, further comprising reducing the phenol concentration of the commercial enzyme preparation comprising the at least one group 3 hydrolase to less than 20 ppm.

18. The method according to claim 16, further comprising reducing the phenol concentration of the commercial enzyme preparation comprising the at least one group 3 hydrolase to less than 10 ppm.

19. The method according to claim 15, wherein the step of reducing the phenol concentration in the feedstock comprises:
passing the feedstock through a chamber containing activated carbon black;
extracting the phenol with 1-hexanol, 1-heptanol, or 1-octanol in combination with an amine mixture and centrifugation; or
using a membrane based separation, wherein ionically and covalently cross-linked ethylene-methacrylic acid copolymers are used.

20. The process according to claim 15, wherein the phenolic compounds are desorbed from the adsorbate or solvent by acetone extraction, and optionally, wherein the desorbed phenolic compounds are further purified by ion exchange, size exclusion, reverse phase or affinity chromatography or a combination of chromatography methods.

21. The method according to claim 11, wherein the step of reducing by at least 1% the phenol concentration of the feedstock is prior to transferring the at least a portion of the phenol-reduced enzyme preparation to the commercial-scale bioreactor.

22. The method according to claim 11, wherein the method further comprises reducing by at least 5% a phenol concentration of the feedstock.

23. The method according to claim 11, wherein the method further comprises reducing by greater than 10% a phenol concentration of the feedstock.

* * * * *